United States Patent [19]

Sullivan et al.

[11] Patent Number: 4,529,124
[45] Date of Patent: Jul. 16, 1985

[54] DEVICE FOR DISPENSING OF VOLATILE SUBSTANCE AND METHOD FOR MAKING THE DEVICE

[75] Inventors: William E. Sullivan, Blythewood; Joseph M. Fore, Batesburg, both of S.C.

[73] Assignee: Risdon Enterprises, Inc., Columbia, S.C.

[21] Appl. No.: 193,356

[22] Filed: Oct. 2, 1980

[51] Int. Cl.³ .............................................. A61L 9/04
[52] U.S. Cl. ..................................................... 239/56
[58] Field of Search ...................... 239/56, 53, 54, 55, 239/57, 60; 206/484, 574.2, 632; 428/43, 905; 156/289, 290; 53/431, 120, 239, 469, 434, 435

[56] References Cited

U.S. PATENT DOCUMENTS

| | | | |
|---|---|---|---|
| 2,626,833 | 1/1953 | Valentine | 239/56 |
| 2,717,174 | 9/1955 | Casanovas | 239/56 |
| 2,979,268 | 4/1961 | Brun | 239/55 |
| 4,094,119 | 6/1978 | Sullivan | 239/56 |
| 4,145,001 | 3/1979 | Weyenberg et al. | 239/56 |
| 4,161,283 | 7/1979 | Hyman | 239/55 |

Primary Examiner—James B. Marbert

Attorney, Agent, or Firm—St. Onge Steward Johnston & Reens

[57] ABSTRACT

An improved device for dispensing a volatile substance into the environment includes a reservoir layer, having opposing first and second surfaces, for holding the substance and first and second envelope layers respectively in close proximity to the first surface and the second surface of the reservoir layer. At least a portion of at least one envelope layer is permeable to the substance. The reservoir layer and envelope layers are fused together at a first generally circular, continuous boundary at which the reservoir layer is nonpermeable to the substance to thereby define a generally circular region within which the substance is confined. The reservoir layer and envelope layers are further fused together at a second non-circular boundary completely enclosing the first boundary and the region to thereby define an outer, decorative, peripheral shape of the device. The device may also include an outer decorative layer in close proximity to at least one of the envelope layers and fused thereto at the second boundary but not at the first whereby the decorative layer has a smooth generally planar outer surface. The decorative layer may carry indicia which is resistant to deterioration caused by the substance.

14 Claims, 4 Drawing Figures

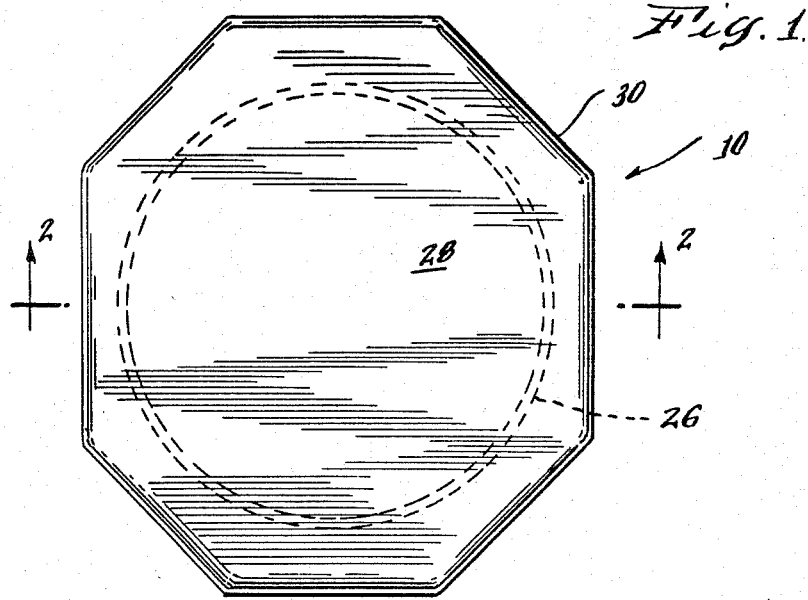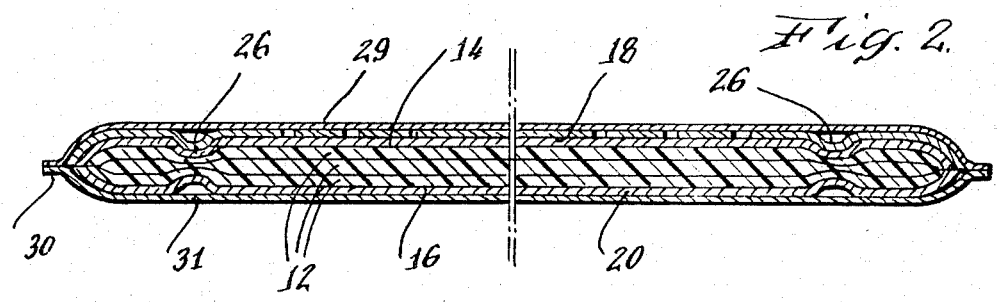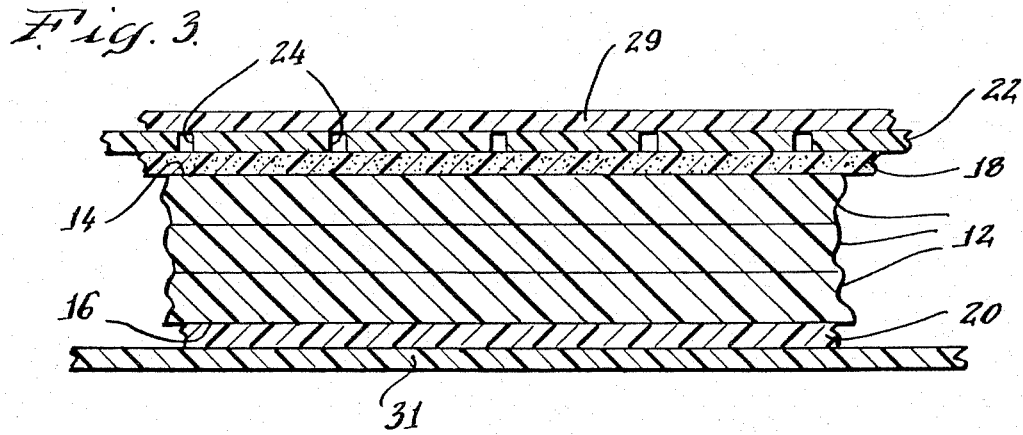

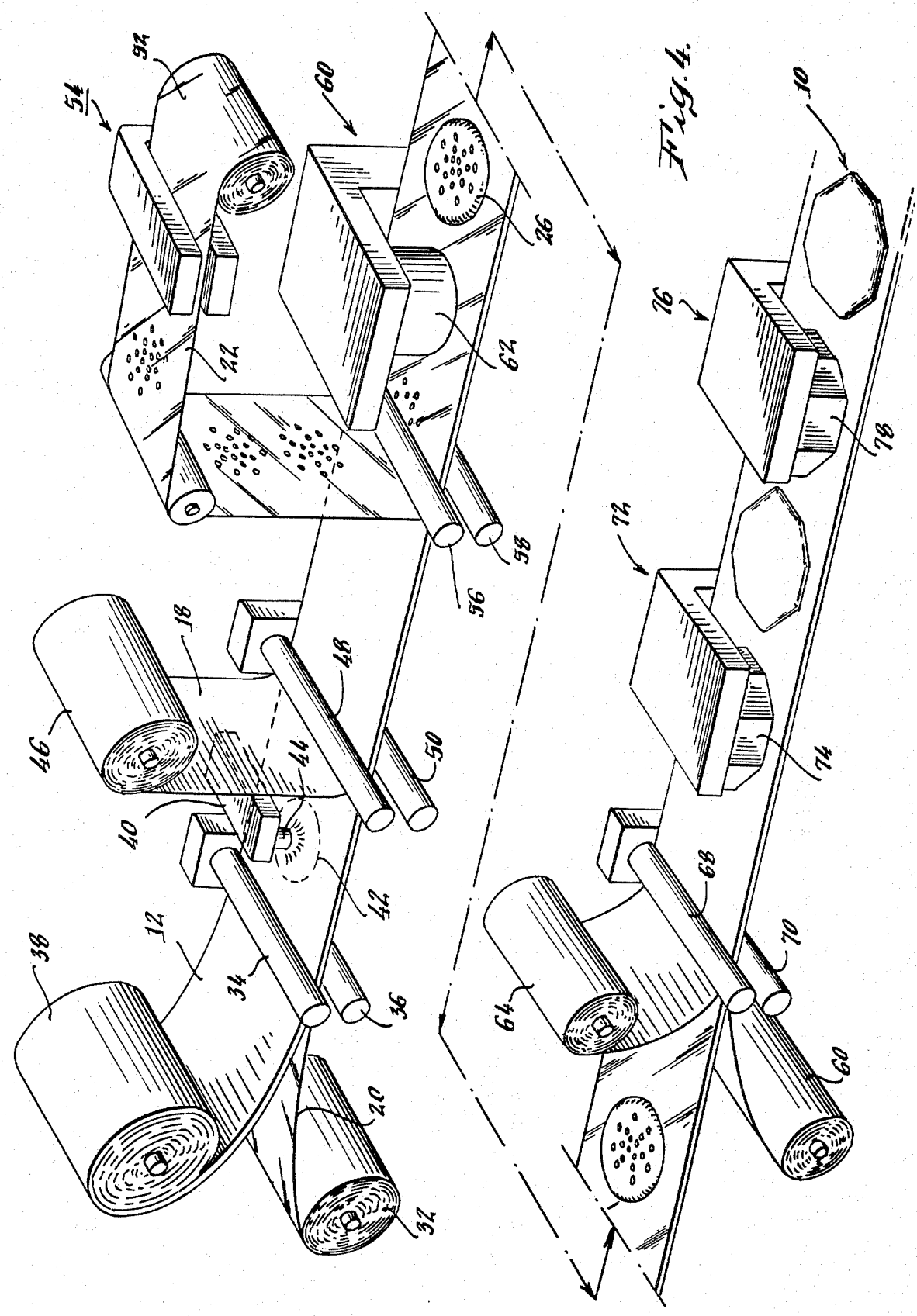

DEVICE FOR DISPENSING OF VOLATILE SUBSTANCE AND METHOD FOR MAKING THE DEVICE

BACKGROUND OF THE INVENTION

1. Field of the Invention

The present invention relates to a device, and to a method of making the device, for dispensing a volatile substance into the environment. In particular, this invention relates to a device and a method of making it in a decorative form that nevertheless is effective to confine the volatile substance and to prevent undesirable dispensing of it in its liquid phase.

Many consumer products such as room deodorizers, insecticides, germicides, fragrances, and the like are volatile and may be released into an area, such as a room, to be treated merely by being exposed therein. Devices for dispensing these products are also available in many forms such as liquid and wick systems, blotter systems, and gel-type systems. However, the volatile substances may be subject to spilling, oozing, or waste in each of these systems. Therefore, various attempts have been made to provide improved devices for dispensing a volatile substance in a controlled manner so that the product is dispensed only in vapor form and undesirable spilling, oozing or waste of the product is avoided.

2. Description of the Prior Art

Various devices and methods for containing a volatile substance and for controlling the release of vapor from the substance are presently known. U.S. Pat. No. 4,158,440 (Sullivan et al), assigned to the assignee of the present invention, discloses a device for releasing a volatile substance that includes a reservoir of substance-absorbent material incapsulated in an envelope, at least a portion of which comprises a permeable material having a porosity at least equal to ultramicroporosity. The permeable envelope portion has a greater affinity for the substance than does the reservoir material. The remainder of the envelope comprises a material impermeable to the substance. Accordingly, the substance permeates through the permeable envelope portion to be released in vapor form into the environment.

U.S. Pat. No. 4,094,199 (Sullivan), also assigned to the assignee of the present invention, discloses a method of making a device for dispensing a volatile substance such as that disclosed in U.S. Pat. No. 4,158,440. This method includes the step of advancing a backing material, a reservoir material and a third material that is permeable to the volatile substance from respective supplies into close proximity to each other, with the reservoir material lying between the backing and permeable materials. The volatile substance is then supplied to the reservoir material to be held thereby. The three materials are fused together in a pattern defining a closed periphery or boundary to seal the reservoir material between the backing and permeable materials at the periphery.

In the method disclosed in the Sullivan et al patent, the fusing step may be performed by an ultrasonic welding apparatus or horn or a heat welding device. It has been learned that it is difficult to reliably form a homogenious seal about a non-circular fused boundary having three or more corners with such apparatus and particularly ultrasonic welding apparatus. It is believed that it is difficult to produce uniform ultrasonic energy about the periphery of a non-circular welding horn. Therefore, it is difficult to concentrate sufficient ultrasonic energy at the corners of a non-circular periphery to form a homogeneous fused seal about the boundary of a dispensing device so produced as is desired. However, homogeneous circular fused boundaries may be reliably made with a circular ultrasonic welding horn because ultrasonic energy may be uniformly distributed about the horn. Therefore, it is preferred that devices made using the method of the Sullivan et al patent have circular shapes. Nevertheless, for aesthetic reasons, it is often desirable to form a dispensing device having a shape other than a circular shape.

It has also been learned that it is desirable to provide a decorative layer on the device to make it more attractive in the environment in which it is used. However, the volatile substances dispensed by devices such as those disclosed in the Sullivan et al patent or made in accordance with the method of the Sullivan patent are often solvents for the inks and dies that may be used to form a decorative image or indicia on the outer layer of such a device. Therefore, when the device is put in use, the inks or dies may run, destroying the original desired indicia or image. The dispensing device and method of making it of the present invention are intended to be improvements to the prior art devices and methods mentioned above.

Still other devices for releasing a volatile substance are disclosed in U.S. Pat. Nos. 3,216,882 (Feldt et al.); 3,770,199 (Hoek et al.); 4,035,451 (Tringali); 2,988,284 (Smith); 3,685,734 (Paciorek et al) and 3,846,404 (Nichols). Other methods and apparatus for making envelopes which are filled with various substances are disclosed in U.S. Pat. Nos. 2,616,232 (Meyer); 2,970,141 (Rohdin); 3,007,848 (Stroop); 3,069,273 (Wayne); 3,495,992 (De For) and 3,978,636 (Clancy).

SUMMARY OF THE INVENTION

In its preferred embodiment, to be described below in detail, the device of the present invention may be formed with a non-circular decorative exterior shape having three or more corners. Nevertheless, this device effectively holds a volatile liquid product against undesirable spilling, waste, or oozing, dispensing the product only in vapor form as desired. Even given these advantages, these devices may be easily and economically made using existing techniques. Further, in its preferred embodiment, the device of the present invention may bear visual images or indicia, for decorative or other purposes, that are not disturbed by common volatile substances carried in the device that are ordinarily solvents for conventional inks or dies. Therefore, both the device and method of the present invention provide great flexibility in meeting the aesthetic demands of the marketplace yet provide an effective dispenser of a volatile substance.

In the preferred embodiment, the device of the present invention includes a reservoir layer, for holding the volatile substance, that has opposing first and second surfaces. First and second envelope layers are mounted respectively in close proximity to the first surface and the second surface of the reservoir layer. At least a portion of at least one of the envelope layers is permeable to the volatile substance.

The reservoir layer and the envelope layers are fused together at a first generally circular, continuous boundary, at which the reservoir layer becomes impermeable to the substance. The boundary thereby defines a generally circular region within which the substance is confined. The reservoir and the envelope layers are also fused together at a second non-circular boundary completely enclosing the first boundary and the region. Accordingly, an outer decorative peripheral shape of the device may be defined independently of the first boundary that confines the substance within the region that it defines.

The device of the invention may further comprise at least one outer decorative layer disposed in close proximity to at least one of the envelope layers and fused to the envelope layers and the reservoir layers at the second boundary but not fused to such layers at the first boundary. Accordingly, the decorative layer has a smooth, generally planar outer surface that masks the first boundary.

The decorative layer is made of a synthetic material that is resistant to deterioration caused by the substance. Indicia such as an attractive design may be applied to the decorative layer and subsequently fused thereto by a heat and pressure transfer process to become a part of the synthetic material of which the decorative layer is made. For example, the indicia may be made of a similar synthetic material and applied to the decorative layer using a process described in greater detail below. In this way, the indicia are uneffected by ordinarily solvent agents carried in the device.

Accordingly, it is an object of the present invention to provide a device for dispensing a volatile substance into the environment which effectively confines the substance in liquid form and prevents the substance from spilling, oozing, or being wasted in that liquid form. This device nevertheless is effective to dispense the product in vapor form and may be made in aestheticly pleasing, decorative shapes that bear attractive images.

It is a further object of the present invention to provide a method for making such a device that is economical and may be implemented using existing technology.

Other objects, aspects and advantages of the present invention will be pointed out in, or all be understood from, the following detailed description provided below in conjunction with the accompanying drawings.

BRIEF DESCRIPTION OF THE DRAWINGS

FIG. 1 is a top plan view of a device constructed in accordance with a preferred embodiment of the present invention. As illustrated, the device has a decorative octagonal shape.

FIG. 2 is a vertical cross-sectional view of the device taken on plane 2—2 in FIG. 1.

FIG. 3 is an enlarged vertical cross-sectional view similar to that shown in FIG. 2 illustrating in detail the various layers of the device of the invention.

FIG. 4 is a diagrammatic illustration of apparatus for making the device of the present invention that is useful to describe the method of the invention.

DETAILED DESCRIPTION OF THE PREFERRED EMBODIMENTS

The figures illustrate one preferred embodiment of the device of the present invention for dispensing a volatile substance, such as a fragrance or deoderizer, into the environment. Specifically, as shown in FIGS. 1 and 2, the device is generally indicated at 10, has an octagonal shape in plan view, and is relatively broad and thin in cross-section. While the device is shown as having an octagonal shape, it may be made in any other attractive non-circular shape, for example, one having three or more generally linear sides and three or more corners in plan view such as a triangle, rectangle, or pentagon. Furthermore, the facing surfaces of the device 10 may be provided with visual images or indicia for decorative or other purposes. The method of providing such indicia will be described in greater detail below.

As shown in detail in FIGS. 2 and 3, the device comprises a reservoir layer 12 that may be in the form of a relatively thick pad or a plurality of thinner pads of material which are capable of absorbing the volatile substance. In the preferred embodiment, this reservoir layer material is highly fibrous, non-woven polypropylene. However, it may be made of any other material which is fusable or weldable, in a manner to be described below in greater detail, that is also absorbent of the volatile substance that the device is intended to hold and dispense.

The reservoir layer has opposing first and second planar surfaces 14 and 16 respectively. Overlying or mounted in close proximity to the first surface is a release layer 18 that is permeable to the volatile substance and is also weldable or fusable. In the preferred embodiment the release layer is a polyolefin diffusion layer. It may, however, be an ultramicroporous material such as a gelled cellulose triacetate film available from Moleculon Research Corporation, microporous polypropylene sold under the trademark "CELGARD" by Celanese Corporation or a ultramicroporous or microporous polyethylene film. In any case, the release layer should be made of a material that is also weldable or fusable with ultrasonic energy or heat.

The device of the invention further includes a lower barrier or envelope layer 20 mounted in close proximity to the reservoir layer that is impermeable to the volatile substance. An upper barrier or envelope layer 22, also impermeable to the volatile substance, overlies or is mounted in close proximity to the release layer 18. Both barrier layers may be made of nonporous polypropylene, for example. The upper barrier layer is provided with a plurality of holes 24, the number and area of which is chosen to yield the desired rate at which the substance is to volatilize. That is, the larger the number and total area of the holes in the upper barrier layer, the larger the surface area of the release layer exposed to the environment and consequently more rapid will be the rate at which the volatile substance is dispensed into the environment. Conversely, the smaller the number and total area of the holes in the upper barrier layer, the lower will be the rate of volatilization.

It will be appreciated that for purposes of this specification and the concluding claims that a portion of at least one envelope layer may be referred to as being permeable to the substance. In the preferred embodiment this portion is formed by the release layer and the perforated upper barrier layer which together define an upper envelope layer, a portion of which is permeable to the substance. However, the release layer alone could constitute an upper envelope layer if desired.

As noted above, all of the materials of which the reservoir, release, and barrier layers are made are weldable or fuseable with ultrasonic energy or heat. Thus, as described in U.S. Pat. No. 4,094,119 (Sullivan) after all are assembled and the volatile product has been introduced into the reservoir layer, all may be fused together in a pattern defining a closed periphery to seal the reservoir material between the extreme barrier layers. The reservoir material is thereby compressed and sealed to prevent lateral transfer of the volatile substance through the fused periphery.

While U.S. Pat. No. 4,094,119 (Sullivan) illustrates a device, for releasing a volatile substance, that is non-circular in plan view, it has been found that there are difficulties in making such devices in such shapes. Specifically, it is difficult to uniformly fuse the respective layers together at corners of a non-circular device using, for example, ultrasonic energy because it is difficult to uniformly distribute ultrasonic energy about the weld boundary of an ultrasonic welding horn. Therefore, the substance may leak from the device at a corner if a sound seal is not formed there. However, ultrasonic energy may be easily uniformly distributed about a circular weld boundary of an ultrasonic welding horn. Accordingly, a reliable circular fused seal about the boundary of the device can be easily formed when a device such as that described above is made with a circular shape.

Other reasons exist, however, for making devices such as these described above in shapes other than circular shapes. For example, it may be desirable to make other such shapes for aesthetic or decorative reasons. In order to satisfy aesthetic requirements and nevertheless produce a device for releasing a volatile substance that reliably confines the substance in its liquid phase to prevent leakage, oozing or spilling, which are of course undesirable, the improved device and method of making it, both in accordance with the invention, have been devised.

Referring again to the FIGS. 1 and 2, the improved device of the invention includes all of the components described above in detail that are first fused together at a generally circular, continuous boundary 26 such that the reservoir layer becomes nonpermeable to the substance at the boundary. Accordingly, the circular boundary defines a generally circular region 28 within which the substance is confined.

In the improved device, the components are then fused together at a second non-circular boundary 30, which is shown in the figures as being octagonal. Of course, any non-circular shape such as an oval or a polygon having three or more sides or corners may be chosen for decorative or aesthetic reasons and may be made. This second non-circular boundary completely encloses the first boundary 26 and the region 28 to thereby define an outer peripheral shape of the device. The first fused boundary creates a reliable seal with existing ultrasonic or heat welding technology through which the volatile substance may not laterally permeate. The second boundary 30 provides a decorative or aesthetically pleasing peripheral shape for the device and need not be uniformly fused so as to prevent lateral permeation by the substance. The second boundary need only have sufficient structural integrity to hold the various layers together. Small imperfections on the sides or at the corners of the second boundary that would otherwise permit the substance to permeate laterally outwardly, can be tolerated since the volatile substance is not nor need it be confined within this second boundary. The first boundary performs this function.

The device of the present invention may also include upper and lower decorative layers 29 and 31 both also made of a fusable material such as woven polyester that has the appearance of cloth. The decorative layers are fused to the remaining layers at the second boundary 30 but not at the first 26. Therefore, the device has smooth generally planar outer surfaces that mask the first boundary 26 to enhance the decorative appearance.

Accordingly, it will be appreciated that while the device of the present invention provides all of the advantages of circular devices of the type described, it also provides the added advantage of a decorative or aesthetically pleasing appearance.

The method of manufacturing the device for dispensing volatile substances described above may be explained with reference to FIG. 4, which diagrammatically illustrates a proposed assembly apparatus. As shown there, lower barrier or envelope layer material is fed between the nip of two drive rollers 34 and 36 from a supply roll 32. A supply roll 38 of reservoir material is mounted above the supply roll 32 and the axes of both rolls are parallel. The reservoir material is fed from the supply roll 38 between the drive rollers 36 and 34 with the lower barrier layer material to be fed to the remaining sections of the apparatus.

The two layers are assembled in congruent fashion between the drive rollers 34 and 36 and passed beneath a filling station 40 which dispenses a fixed quantity of the volatile substance onto the reservoir layer. As shown in FIG. 4, the substance is dispensed from a nozzle 44 depending at the filling station 40 generally at a laterally central location on the strip of assembled barrier and reservoir layers and spreads out or is absorbed in a circular pattern shown at 42. Thereafter, the reservoir and lower barrier layers are assembled with the release layer 18 that is payed from a supply 46. A second pair of drive rollers 48 and 50 are provided to advance the now three assembled layers and urge them together. The upper barrier layer 22 is fed from a supply roll 52 through a punching station, generally indicated at 54, that perforates the upper barrier layer in a desired pattern and to a desired total area. The upper barrier layer is then assembled with the three previously assembled layers between the nip of a third pair of drive rollers 56 and 58 so that the punched pattern of holes in the upper barrier layer overlies a circular pattern of substance now carried in the reservoir layer.

A fusing station, generally indicated at 60, fuses the upper barrier layer, the release layer, the reservoir layer and the lower barrier layer together at the first circular boundary 26 about the pattern of holes in the upper barrier layer and the substance. This fusing station may comprise a sonic welding horn 62, having a circular weld boundary that is mounted to move toward and away from the assembled layers to compress and fuse them together in a well known manner. As noted above, however, the fusing station may alternatively comprise a heat applying horn, having circular weld boundary or other apparatus for fusing the four assembled layers together about the circular boundary.

The circular boundary formed by the fused layers acts to prevent further lateral absorption by the reservoir layer of the volatile substance. Moreover, because the pattern is circular, weaknesses that might exist at the corners of non-circular boundaries are eliminated and oozing, spilling or waste of the volatile substance through the circular boundary is effectively eliminated.

The continuous assembled strip now having a series of fused circular boundaries defining a plurality of devices on it is then fed to a position between two supply rolls 64 and 66 of decorative layer material. The respective decorative layers are fed into close proximity to the top and bottom of the remaining assembled layers between a fourth pair of drive rollers 68 and 70. All assembled layers are then fed to a second fusing station, generally indicated at 72, that comprises a sonic welding horn 74 having a weld boundary shape of that desired for the finished device. The fusing station may alternatively comprise a heat applying horn. As illustrated with reference to the preferred embodiment, this shape is, of course, octagonal. The sonic welding horn 74 has dimensions that are sufficient to form a second boundary completely enclosing the first circular boundary formed by the sonic welding horn 62 of fusing station 60. The assembled layers are fed to the fusing station 72 so that the first circular boundary is properly registered within and completely contained within the boundary formed by the sonic welding horn 74 at the second fusing station 72.

After the final fusing step, all assembled layers are fed to a punching station 76 that includes a cutting horn 78 having a shape congruent to and slightly larger than the boundary formed by the sonic welding horn 74. The finished device is accordingly punched from the remainder of the strip by the severing station 76 for ultimate use.

It will be appreciated that the method of manufacturing the device of the present invention, the steps of which may be performed by an apparatus such as that described above, provides all of the advantages of the device and further provides economical assembly with existing technology. It will further be appreciated that while a diagrammatic representation of apparatus for assembling the device has been offered above, many variations of actual apparatus for performing the various steps of the method may be envisioned.

The device for dispensing a volatile product in the present invention may also bear decorative images. It has been learned that many volatile substances that are dispensed from a device such as the type described are solvents for printing inks that ordinarily might be used to apply an image or indicia to such a device. In accordance with the present invention, a technique has been adopted for avoiding this problem. In particular, an image is applied to one or both of the decorative layers, 29 and 31, using a known heat transfer or sublimation printing process. Specifically, the decorative layers comprise a heat weldable or fuseable material such as woven polyester that may have the appearance of cloth. An image is then first applied to a transfer sheet or paper and is printed with heat transfer or sublimation type ink that is also fuseable. Thereafter, the transfer paper is placed in contact with the surface of the decorative layer and heat and pressure are applied thereto. The heat and presure causes the ink to be transferred into and become an integral part of the polyester fabric by a mass-transfer process. It has been found that when the pressure and heat are removed from the paper and fabric and the paper and fabric are separated, the decorative image becomes a permanent part of the fabric which is impervious to and unaffected by common volatile products which are dispensed by the device of the invention. Accordingly, problems of running or other destruction of the image or indicia are avoided.

The apparatus of the invention shown in FIG. 4 may include a station for printing such images on the decorative fabrics or the images may be supplied to the decorative fabrics prior to being placed on the apparatus shown in FIG. 4. Orchard Corporation of America, St. Louis Mo., is one company that manufactures printed transfer sheets with images that are used in the heat transfer or sublimation printing process. Caro Print, Spartanburg, S.C., is one company that actually practices this process in the manner generally described above.

Accordingly, although specific embodiments of the present invention have been described above in detail, it is to be understood that this is for purposes of illustration. Modification may be made to the described method and apparatus for releasing a volatile substance into the environment without others skilled in the art.

We claim:

1. In a device for dispensing a volatile substance into the environment including a continuous sheet-like reservoir layer for holding the substance and having opposing first and second surfaces, and first and second continuous, sheet-like envelope layers respectively in close proximity to said first surface and said second surface of said reservoir layer, at least a portion of at least one envelope layer being permeable to said substance; the improvement in which:

said reservoir layer and said envelope layers are fused together at a generally circular, continuous boundary, at which said reservoir layer is impermeable to said substance, thereby defining a generally circular region within which said substance is confined; and in which said reservoir layer and said envelope layers are fused together at a second non-circular boundary completely enclosing said first boundary and said region and thereby defining an outer, decorative, peripheral shape of said device; and in which device further comprises:

at least one continuous, sheet-like outer decorative layer in close proximity to at least one of said envelope layers, fused to said envelope layers and said reservoir layer at said second boundary, said decorative layer being made of material resistant to deterioration caused by said substance and carrying indicia that form an integral part thereof, which are thereby also resistant to deterioration caused by said substance.

2. The improvement in a device for dispensing a volatile substance as claimed in claim 1 wherein said decorative layer is not fused to said envelope layers and said reservoir layer at said first boundary, whereby said decorative layer has a smooth, generally planar outer surface within said second boundary.

3. The improvement in a device for dispensing a volatile substance as claimed in claim 2 wherein said device further comprises a second continuous, sheet-like outer decorative layer in close proximity to the other of said first and second envelope layers and fused to said envelope layers and said reservoir layer at said second boundary, said second decorative layer also being made of a material resistant to deterioration caused by said substance and carrying indicia that form an integral part thereof which are thereby also resistant to deterioration caused by said substance.

4. The improvement in a device for dispensing a volatile substance as claimed in claim 3 wherein neither of said decorative layers are fused to said envelope layers and said reservoir layer at said first boundary, whereby said decorative layers have smooth, generally planar outer surfaces within said second boundary.

5. The improvement in a device for dispensing a volatile substance as claimed in claims 2, 3 or 4 wherein said indicia are fused to said decorative layer by a heat-transfer printing process.

6. The improvement in a device for dispensing a volatile substance as claimed in claims 2, 3 or 4 wherein said decorative layer is made of a fibrous, woven material resistant to deterioration caused by said substance.

7. The improvement in a device for dispensing a volatile substance as claimed in claims 2, 3 or 4 wherein said material of which a decorative layer is made is a polyester.

8. The improvement in a device for dispensing a volatile substance as claimed in claim 1 wherein said second boundary comprises at least three generally linear sides and at least three corners.

9. A method of producing a device for dispensing of a volatile substance into the environment, comprising the steps of:

providing a continuous, sheet-like reservoir layer made of a material capable of holding said substance and having opposing first and second surfaces;

supplying said substance to said reservoir layer to be held thereby;

placing a first continuous, sheet-like reservoir envelope layer in close proximity to said first surface of said reservoir layer;

placing a second continuous, sheet-like envelope layer in close proximity to said second surface of said reservoir layer, at least a portion of at least one of said envelope layers being permeable to said substance;

providing at least one continuous, sheet-like outer decorative layer made of a material resistant to deterioration caused by said substance;

printing indicia on said decorative layer to thereby form an integral part thereof and thereby also be resistant to deterioration caused by said substance;

first fusing said reservoir layers and said envelope layers together at a first generally circular, continuous boundary enclosing said substance, at which said reservoir layer is impermeable to said substance, to thereby define a generally circular region within which said substance is confined; and placing said decorative layer in close proximity to at least one of said envelope layers; and second fusing said reservoir layer, said envelope layers, and said decorative layer together at a second non-circular boundary completely enclosing said first boundary and said region to thereby define an outer decorative, peripheral shape of said device and to thereby define at least one smooth, generally planar outer surface of said device.

10. The method as claimed in claim 9 wherein said second fusing step comprises fusing said reservoir layer, said envelope layers and said decorative layers together at said second boundary to also enclose said indicia on said decorative layers.

11. The method as claimed in claim 9 wherein said printing and indicia fusing steps comprise heat-transfer printing said indicia on said decorative layers.

12. The method as claimed in claim 9 wherein said second fusing step comprises:

fusing said layers at said second boundary with at least three generally linear sides and at least three corners.

13. The method as claimed in claim 11 wherein said heat transfer printing step comprises:

printing said indicia on a transfer sheet;

placing said transfer sheet on said decorative layer with said indicia in contact therewith; and applying heat and pressure to said transfer sheet and said decorative layer to cause said indicia to become an integral part of said decorative layer by a mass transfer process.

14. The method as claimed in claim 9 further comprising the steps of:

providing a second outer decorative layer;

placing said second decorative layer in close proximity to the other of said envelope layers and wherein said second fusing step comprises:

also fusing said second decorative layer to said other layers at said second boundary.

* * * * *